US008560036B2

(12) United States Patent  
Baker, Jr.

(10) Patent No.: US 8,560,036 B2
(45) Date of Patent: *Oct. 15, 2013

(54) SELECTION OF ENSEMBLE AVERAGING WEIGHTS FOR A PULSE OXIMETER BASED ON SIGNAL QUALITY METRICS

(75) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 348 days.

This patent is subject to a terminal disclaimer.

(21) Appl. No.: 12/979,828

(22) Filed: Dec. 28, 2010

(65) Prior Publication Data

US 2011/0092785 A1 Apr. 21, 2011

Related U.S. Application Data

(63) Continuation of application No. 12/315,449, filed on Dec. 3, 2008, now Pat. No. 7,890,154, which is a continuation of application No. 11/701,173, filed on Feb. 1, 2007, now Pat. No. 7,474,907, which is a continuation of application No. 10/796,559, filed on Mar. 8, 2004, now Pat. No. 7,194,293.

(51) Int. Cl.
*A61B 5/1455* (2006.01)

(52) U.S. Cl.
USPC .......................................................... 600/336

(58) Field of Classification Search
USPC ................... 600/310, 322, 323, 336
See application file for complete search history.

(56) References Cited

U.S. PATENT DOCUMENTS

| | | |
|---|---|---|
| 3,638,640 A | 2/1972 | Shaw |
| 3,647,299 A | 3/1972 | Lavallee |
| 3,704,706 A | 12/1972 | Herczfeld et al. |
| 4,063,551 A | 12/1977 | Sweeney |
| 4,086,915 A | 5/1978 | Kofsky et al. |
| 4,095,117 A | 6/1978 | Nagy |
| 4,266,554 A | 5/1981 | Hamaguri |
| 4,407,290 A | 10/1983 | Wilber |
| 4,537,200 A | 8/1985 | Widrow |
| 4,549,551 A | 10/1985 | Dyck et al. |
| 4,603,700 A | 8/1986 | Nichols et al. |
| 4,621,643 A | 11/1986 | New, Jr. et al. |
| 4,649,505 A | 3/1987 | Zinser, Jr. et al. |
| 4,700,708 A | 10/1987 | New, Jr. et al. |
| 4,705,049 A | 11/1987 | John |

(Continued)

FOREIGN PATENT DOCUMENTS

| | | |
|---|---|---|
| DE | 19640807 | 9/1997 |
| EP | 0630203 | 9/1993 |

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Eric Winakur
(74) *Attorney, Agent, or Firm* — Fletcher Yoder, P.C.

(57) ABSTRACT

A pulse oximeter system is presently disclosed. The pulse oximeter system includes a processor and circuitry. The processor and circuitry are configured to receive light waveforms from a sensor, determine at least one signal quality metric for the light waveforms, calculate at least one weight using a continuously variable weighting function based on the at least one signal quality metric, and ensemble average the light waveforms using the at least one calculated weight.

20 Claims, 2 Drawing Sheets

(56) References Cited

U.S. PATENT DOCUMENTS

| | | |
|---|---|---|
| 4,714,341 A | 12/1987 | Hamaguri et al. |
| 4,723,294 A | 2/1988 | Taguchi |
| 4,763,282 A | 8/1988 | Rosenberg |
| 4,770,179 A | 9/1988 | New, Jr. et al. |
| 4,773,422 A | 9/1988 | Isaacson et al. |
| 4,799,493 A | 1/1989 | DuFault |
| 4,800,495 A | 1/1989 | Smith |
| 4,802,486 A | 2/1989 | Goodman et al. |
| 4,805,623 A | 2/1989 | Jöbsis |
| 4,807,631 A | 2/1989 | Hersh et al. |
| 4,817,013 A | 3/1989 | Corenman et al. |
| 4,819,752 A | 4/1989 | Zelin |
| 4,824,242 A | 4/1989 | Frick et al. |
| 4,848,901 A | 7/1989 | Hood, Jr. |
| 4,860,759 A | 8/1989 | Kahn et al. |
| 4,863,265 A | 9/1989 | Flower et al. |
| 4,867,571 A | 9/1989 | Frick et al. |
| 4,869,253 A | 9/1989 | Craig, Jr. et al. |
| 4,869,254 A | 9/1989 | Stone et al. |
| 4,883,353 A | 11/1989 | Hausman et al. |
| 4,892,101 A | 1/1990 | Cheung et al. |
| 4,907,594 A | 3/1990 | Muz |
| 4,911,167 A | 3/1990 | Corenman et al. |
| 4,913,150 A | 4/1990 | Cheung et al. |
| 4,927,264 A | 5/1990 | Shiga et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,948,248 A | 8/1990 | Lehman |
| 4,949,710 A | 8/1990 | Dorsett et al. |
| 4,955,379 A | 9/1990 | Hall |
| 4,956,867 A | 9/1990 | Zurek et al. |
| 4,958,638 A | 9/1990 | Sharpe et al. |
| 4,960,126 A | 10/1990 | Conlon et al. |
| 4,971,062 A | 11/1990 | Hasebe et al. |
| 4,972,331 A | 11/1990 | Chance |
| 4,972,842 A | 11/1990 | Korten et al. |
| 4,974,591 A | 12/1990 | Awazu et al. |
| 5,025,791 A | 6/1991 | Niwa |
| 5,028,787 A | 7/1991 | Rosenthal et al. |
| 5,054,495 A | 10/1991 | Uemura et al. |
| 5,057,695 A | 10/1991 | Hirao et al. |
| 5,058,588 A | 10/1991 | Kaestle |
| 5,065,749 A | 11/1991 | Hasebe et al. |
| 5,078,136 A | 1/1992 | Stone et al. |
| 5,084,327 A | 1/1992 | Stengel |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,002 A | 9/1993 | Prosser |
| 5,246,003 A | 9/1993 | DeLonzor |
| 5,247,931 A | 9/1993 | Norwood |
| 5,263,244 A | 11/1993 | Centa et al. |
| 5,267,562 A | 12/1993 | Ukawa et al. |
| 5,273,036 A | 12/1993 | Kronberg et al. |
| 5,275,159 A | 1/1994 | Griebel |
| 5,279,295 A | 1/1994 | Martens et al. |
| 5,285,782 A | 2/1994 | Prosser |
| 5,297,548 A | 3/1994 | Pologe |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,372,136 A | 12/1994 | Steuer et al. |
| 5,385,143 A | 1/1995 | Aoyagi |
| 5,390,670 A | 2/1995 | Centa et al. |
| 5,398,680 A | 3/1995 | Polson et al. |
| 5,398,682 A | 3/1995 | Lynn |
| 5,413,099 A | 5/1995 | Schmidt et al. |
| 5,431,170 A | 7/1995 | Mathews |
| 5,458,128 A | 10/1995 | Polanyi et al. |
| 5,467,778 A | 11/1995 | Catt et al. |
| 5,469,845 A | 11/1995 | DeLonzor et al. |
| RE35,122 E | 12/1995 | Corenman et al. |
| 5,479,922 A | 1/1996 | Reichl |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,494,032 A | 2/1996 | Robinson et al. |
| 5,503,148 A | 4/1996 | Pologe et al. |
| 5,511,042 A | 4/1996 | O'Brien, Jr. |
| 5,524,617 A | 6/1996 | Mannheimer |
| 5,524,631 A | 6/1996 | Zahorian et al. |
| 5,553,614 A | 9/1996 | Chance |
| 5,553,615 A | 9/1996 | Carim et al. |
| 5,564,417 A | 10/1996 | Chance |
| 5,575,284 A | 11/1996 | Athan et al. |
| 5,575,285 A | 11/1996 | Takanashi et al. |
| 5,588,439 A | 12/1996 | Hollub |
| 5,605,151 A | 2/1997 | Lynn |
| 5,611,337 A | 3/1997 | Bukta |
| 5,630,413 A | 5/1997 | Thomas et al. |
| 5,632,272 A | 5/1997 | Diab et al. |
| 5,645,059 A | 7/1997 | Fein et al. |
| 5,645,060 A | 7/1997 | Yorkey |
| 5,676,141 A | 10/1997 | Hollub |
| 5,680,857 A | 10/1997 | Pelikan et al. |
| 5,685,299 A | 11/1997 | Diab et al. |
| 5,692,503 A | 12/1997 | Kuenstner |
| 5,730,124 A | 3/1998 | Yamauchi |
| 5,743,263 A | 4/1998 | Baker, Jr. |
| 5,746,206 A | 5/1998 | Mannheimer |
| 5,758,644 A | 6/1998 | Diab et al. |
| 5,769,785 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,820,550 A | 10/1998 | Polson et al. |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,853,364 A | 12/1998 | Baker et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,934,277 A | 8/1999 | Mortz |
| 5,995,855 A | 11/1999 | Kiani et al. |
| 5,995,856 A | 11/1999 | Mannheimer et al. |
| 5,995,859 A | 11/1999 | Takahashi |
| 6,002,952 A | 12/1999 | Diab et al. |
| 6,011,986 A | 1/2000 | Diab et al. |
| 6,064,898 A | 5/2000 | Aldrich |
| 6,081,735 A | 6/2000 | Diab et al. |
| 6,081,742 A | 6/2000 | Amano et al. |
| 6,083,157 A | 7/2000 | Noller |
| 6,088,607 A | 7/2000 | Diab et al. |
| 6,094,592 A | 7/2000 | Yorkey et al. |
| 6,120,460 A | 9/2000 | Abreu |
| 6,134,460 A | 10/2000 | Chance |
| 6,150,951 A | 11/2000 | Olejniczak |
| 6,151,518 A | 11/2000 | Hayashi |
| 6,154,667 A | 11/2000 | Miura et al. |
| 6,157,850 A | 12/2000 | Diab et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,236,872 B1 | 5/2001 | Diab et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,339,715 B1 | 1/2002 | Bahr et al. |
| 6,353,750 B1 | 3/2002 | Kimura et al. |
| 6,360,114 B1 | 3/2002 | Diab et al. |
| 6,385,471 B1 | 5/2002 | Mortz |
| 6,397,091 B2 | 5/2002 | Diab et al. |
| 6,408,198 B1 | 6/2002 | Hanna et al. |
| 6,415,236 B2 | 7/2002 | Kobayashi et al. |
| 6,419,671 B1 | 7/2002 | Lemberg |
| 6,430,525 B1 | 8/2002 | Weber et al. |

(56) References Cited

U.S. PATENT DOCUMENTS

| | | |
|---|---|---|
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,505,060 B1 | 1/2003 | Norris |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,647,280 B2 | 11/2003 | Bahr et al. |
| 6,650,918 B2 | 11/2003 | Terry |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,721,584 B2 | 4/2004 | Baker et al. |
| 6,731,274 B2 | 5/2004 | Powell |
| 6,745,060 B2 | 6/2004 | Diab et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,810,277 B2 | 10/2004 | Edgar, Jr. et al. |
| 6,829,496 B2 | 12/2004 | Nagai et al. |
| 6,836,679 B2 | 12/2004 | Baker, Jr. et al. |
| 6,839,582 B2 | 1/2005 | Heckel |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,987,994 B1 | 1/2006 | Mortz |
| 6,993,371 B2 | 1/2006 | Kiani et al. |
| 6,996,427 B2 | 2/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,039,538 B2 | 5/2006 | Baker, Jr. |
| 7,047,056 B2 | 5/2006 | Hannula et al. |
| 7,127,278 B2 | 10/2006 | Melker et al. |
| 7,139,599 B2 | 11/2006 | Terry |
| 7,162,306 B2 | 1/2007 | Caby et al. |
| 7,209,774 B2 | 4/2007 | Baker, Jr. |
| 7,209,775 B2 | 4/2007 | Bae et al. |
| 7,236,811 B2 | 6/2007 | Schmitt |
| 7,263,395 B2 | 8/2007 | Chan et al. |
| 7,272,426 B2 | 9/2007 | Schmid |
| 7,373,193 B2 | 5/2008 | Al-Ali et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0137994 A1 | 9/2002 | Baker et al. |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0009091 A1 | 1/2003 | Edgar, Jr. et al. |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0039273 A1 | 2/2004 | Terry |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0158135 A1 | 8/2004 | Baker et al. |
| 2004/0171920 A1 | 9/2004 | Mannheimer et al. |
| 2004/0171948 A1 | 9/2004 | Terry |
| 2004/0176670 A1 | 9/2004 | Takamura et al. |
| 2004/0176671 A1 | 9/2004 | Fine et al. |
| 2004/0181134 A1 | 9/2004 | Baker et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0197552 A1 | 9/2005 | Baker, Jr. |
| 2005/0197793 A1 | 9/2005 | Baker, Jr. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0195280 A1 | 8/2006 | Baker, Jr. |
| 2006/0224058 A1 | 10/2006 | Mannheimer |
| 2006/0247501 A1 | 11/2006 | Ali |
| 2006/0258921 A1 | 11/2006 | Addison et al. |

FOREIGN PATENT DOCUMENTS

| | | |
|---|---|---|
| EP | 1006863 | 10/2003 |
| JP | 3170866 | 7/1991 |
| JP | 3238813 | 10/1991 |
| JP | 4191642 | 7/1992 |
| JP | 4332536 | 11/1992 |
| JP | 5049624 | 3/1993 |
| JP | 6016774 | 1/1994 |
| JP | 7124138 | 5/1995 |
| JP | 10216115 | 8/1998 |
| JP | 10337282 | 12/1998 |

(56) References Cited

FOREIGN PATENT DOCUMENTS

| | | |
|---|---|---|
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| JP | 2005095606 | 4/2005 |
| WO | WO9221281 | 12/1992 |
| WO | WO9309711 | 5/1993 |
| WO | WO9403102 | 2/1994 |
| WO | WO9512349 | 5/1995 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO2005009221 | 2/2005 |

OTHER PUBLICATIONS

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.

Such, Hans Olaf; "Optoelectronic Non-invasive Vascular Diagnostics Using multiple Wavelength and Imaging Approach," Dissertation, (1998).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Johansson, A.; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," Proceedings of the 26th Annual International conference of the IEEE EMBS, San Francisco, California, Sep. 2004, pp. 2153-2156.

Matsuzawa, Y., et al.; "Pulse Oximeter," *Home Care Medicine*, pp. 42-45 (Jul. 2004); (Article in Japanese—contains English summary of article).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Huang, J., et al.; "Low Power Motion Tolerant Pulse Oximetry," *Abstracts*, A7, p. S103 (undated).

Lang, P., et al.; "Signal Identification and Quality Indicator™ for Motion Resistant Pulse Oximetry," *Abstracts*, A10, p. 5105 (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," Journal of Oral Cavity Medicine, vol. 69, No. 4, pp. 53 (date unknown) (Article in Japanese—contains English summary of article).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Neumann, R., et al.; "Fourier Artifact Suppression Technology Provides Reliable $SpO_2$," *Abstracts*, A11, p. S105 (undated).

SELECTION OF ENSEMBLE AVERAGING WEIGHTS FOR A PULSE OXIMETER BASED ON SIGNAL QUALITY METRICS

This application is a continuation of U.S. patent application Ser. No. 12/315,449, filed Dec. 3, 2008, which is a continuation of U.S. patent application Ser. No. 11/701,173, filed on Feb. 1, 2007, now U.S. Pat. No. 7,474,907 issued Jan. 6, 2009, which is a continuation of U.S. patent application Ser. No. 10/796,559, filed on Mar. 8, 2004, now U.S. Pat. No. 7,194,293 issued Mar. 20, 2007, the full disclosures of which are hereby incorporated by reference in their entirety.

BACKGROUND OF THE INVENTION

The present invention relates in general to oximeters, and in particular to the selection of ensemble averaging weights used for ensemble averaging of signals that include detected waveforms from a pulse oximeter.

A pulse oximeter is typically used to measure various blood characteristics including the blood oxygen saturation of hemoglobin in arterial blood and the pulse rate of the patient. Measurement of these characteristics has been accomplished by use of a non-invasive sensor that passes light through a portion of a patient's blood perfused tissue and photo-electrically senses the absorption and scattering of light in such tissue. The amount of light absorbed and scattered is then used to estimate the amount of blood constituent in the tissue using various algorithms known in the art. The "pulse" in pulse oximetry comes from the time varying amount of arterial blood in the tissue during a cardiac cycle. The signal processed from the sensed optical measurement is the familiar plethysmographic waveform, which corresponds with the cyclic attenuation of optical energy through a portion of a patient's blood perfused tissue.

Ensemble averaging, which is a temporal averaging scheme, involves the use of weighting factors. In a pulse oximeter, ensemble averaging is used to calculate a weighted average of new samples and previous ensemble-averaged samples from one pulse-period earlier. Weights selected and/or used for ensemble averaging have a significant effect on the ensemble averaging process. Such weights may be uniformly selected, or they may be based on the characteristics of the signals that are being ensemble averaged. For example, the Conlon U.S. Pat. No. 4,960,126 discloses ensemble averaging where different weights are assigned to different pulses and a composite, averaged pulse waveform is used to calculate oxygen saturation. Conlon's signal metrics for adjusting ensemble-averaging weights are based on a measure of the degree of motion artifact, a measure of the degree of low perfusion (e.g., pulse amplitude below a threshold), and pulse rate.

However, it is desirable to provide a more flexible and more robust methodology for the selection of ensemble averaging weights used for ensemble averaging of signals that include detected waveforms from a pulse oximeter.

BRIEF SUMMARY OF THE INVENTION

The present invention is directed to the selection of ensemble averaging weights used for ensemble averaging of signals that correspond with detected waveforms from a pulse oximeter. The selection of ensemble averaging weights are based on one or more or a combination of various signal quality metrics or indicators. In one embodiment, the present invention provides a method of ensemble averaging signals in a pulse oximeter. The method includes receiving first and second electromagnetic radiation signals from a blood perfused tissue portion corresponding to two different wavelengths of light; obtaining an assessment of the signal quality of the electromagnetic signals; selecting weights for an ensemble averager using the assessment of signal quality; and ensemble averaging the electromagnetic signals using the ensemble averager.

In one aspect, the selection of ensemble averaging weights involves an assessment and use of various signal quality indicators, where the selecting of weights includes forming a combination of one or more of the following signal quality parameters, namely: a measure of the degree of arrhythmia of the signals; a measure of the degree of similarity or correlation between the first and second electromagnetic radiation signals; a measure of the degree of motion artifact by obtaining a ratio of a current pulse amplitude to the long-term average pulse amplitude of the signals; a ratio of a current pulse amplitude to the previous pulse amplitude of the signal; and a ratio of a current pulse period to that of an average pulse period of the signals.

For a fuller understanding of the nature and advantages of the embodiments of the present invention, reference should be made to the following detailed description taken in conjunction with the accompanying drawings.

DETAILED DESCRIPTION OF THE INVENTION

The methods and systems in accordance with the embodiments of the present invention are directed towards the selection of ensemble averaging weights used for ensemble averaging of signals that correspond with detected waveforms from a pulse oximeter. The selection of ensemble averaging weights are based on one or more or a combination of various signal quality metrics or indicators. The embodiments of the present invention are particularly applicable to and will be explained by reference to measurements of oxygen saturation of hemoglobin in arterial blood and pulse or heart rate, as in pulse oximeter monitors and pulse oximetry sensors. However, it should be realized that the embodiments of the present invention are equally applicable to any generalized patient monitor and associated patient sensor, such as ECG, blood pressure, etc., and are thus also applicable to non oximetry or pulse oximetry devices.

A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared (IR) signals. This modulation ratio has been observed to correlate well to arterial oxygen saturation. Pulse oximeters and sensors may be empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPA- RATUS FOR ESTIMATING PHYSIOLOGICAL PARAMETERS USING MODEL-BASED ADAPTIVE FILTERING," issued Dec. 29, 1998, and U.S. Pat. No. 4,911,167, entitled "METHOD AND APPARATUS FOR DETECTING OPTICAL PULSES," issued Mar. 27, 1990, which are both herein incorporated by reference in their entirety for all purposes. The relationship between oxygen saturation and modulation ratio is described, for example, in U.S. Pat. No. 5,645,059, entitled "MEDICAL SENSOR WITH MODULATED ENCODING SCHEME," issued Jul. 8, 1997, which is herein incorporated by reference in its entirety for all purposes. Most pulse oximeters extract the plethysmographic signal having first determined saturation or pulse rate, both of which are susceptible to interference.

Figure 1:
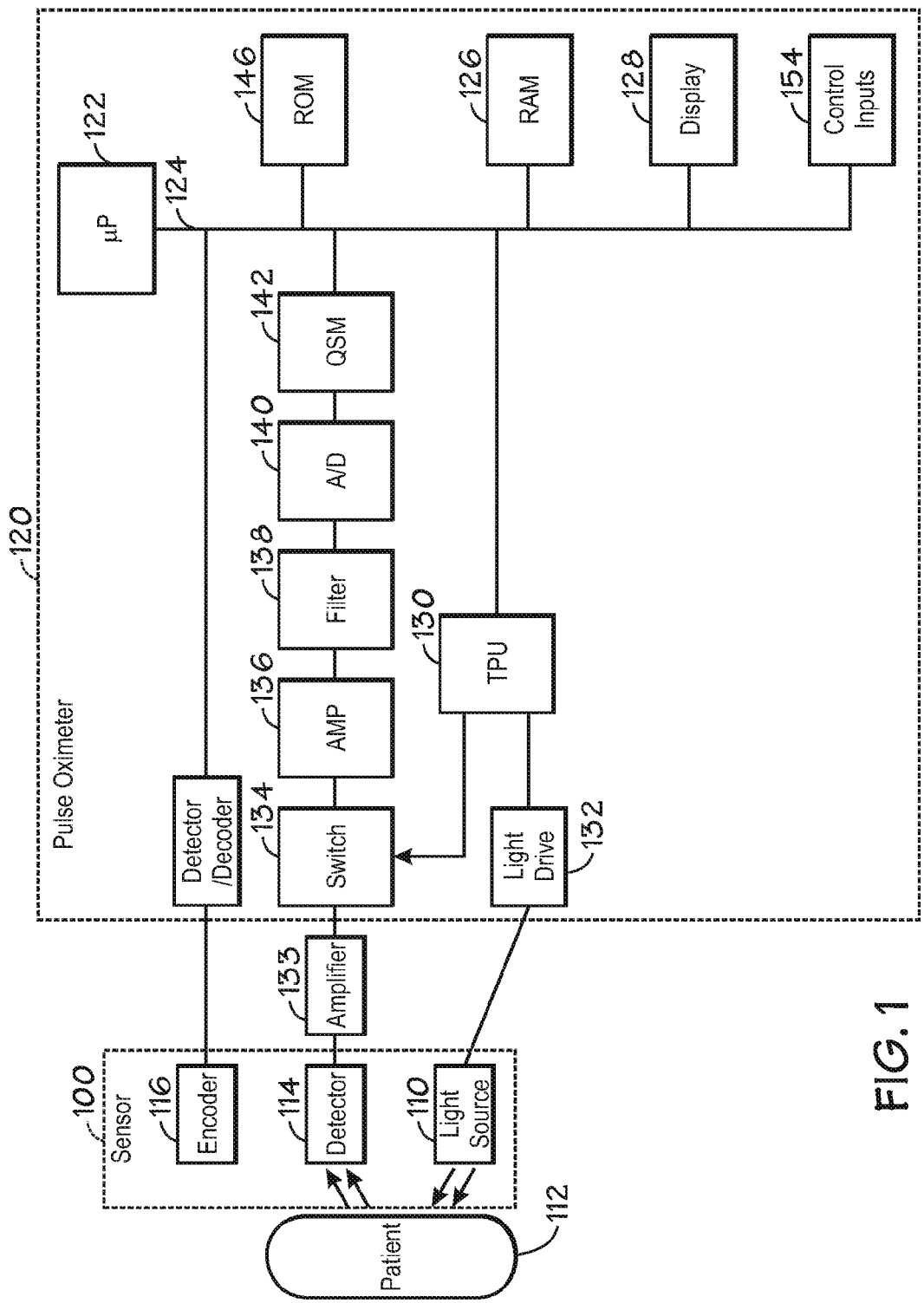
FIG. 1 is a block diagram of an exemplary oximeter.

FIG. 1 is a block diagram of one embodiment of a pulse oximeter that may be configured to implement the embodiments of the present invention. The embodiments of the present invention may be implemented as a data processing algorithm that is executed by the microprocessor 122, described below. Light from light source 110 passes into a blood perfused tissue 112, and is scattered and detected by photodetector 114. A sensor 100 containing the light source and photodetector may also contain an encoder 116 which provides signals indicative of the wavelength of light source 110 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus is a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier, filter and A/D converters for multiple light wavelengths or spectra received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. In a two-wavelength system, the particular set of coefficients chosen for any pair of wavelength spectra is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

Figure 2:
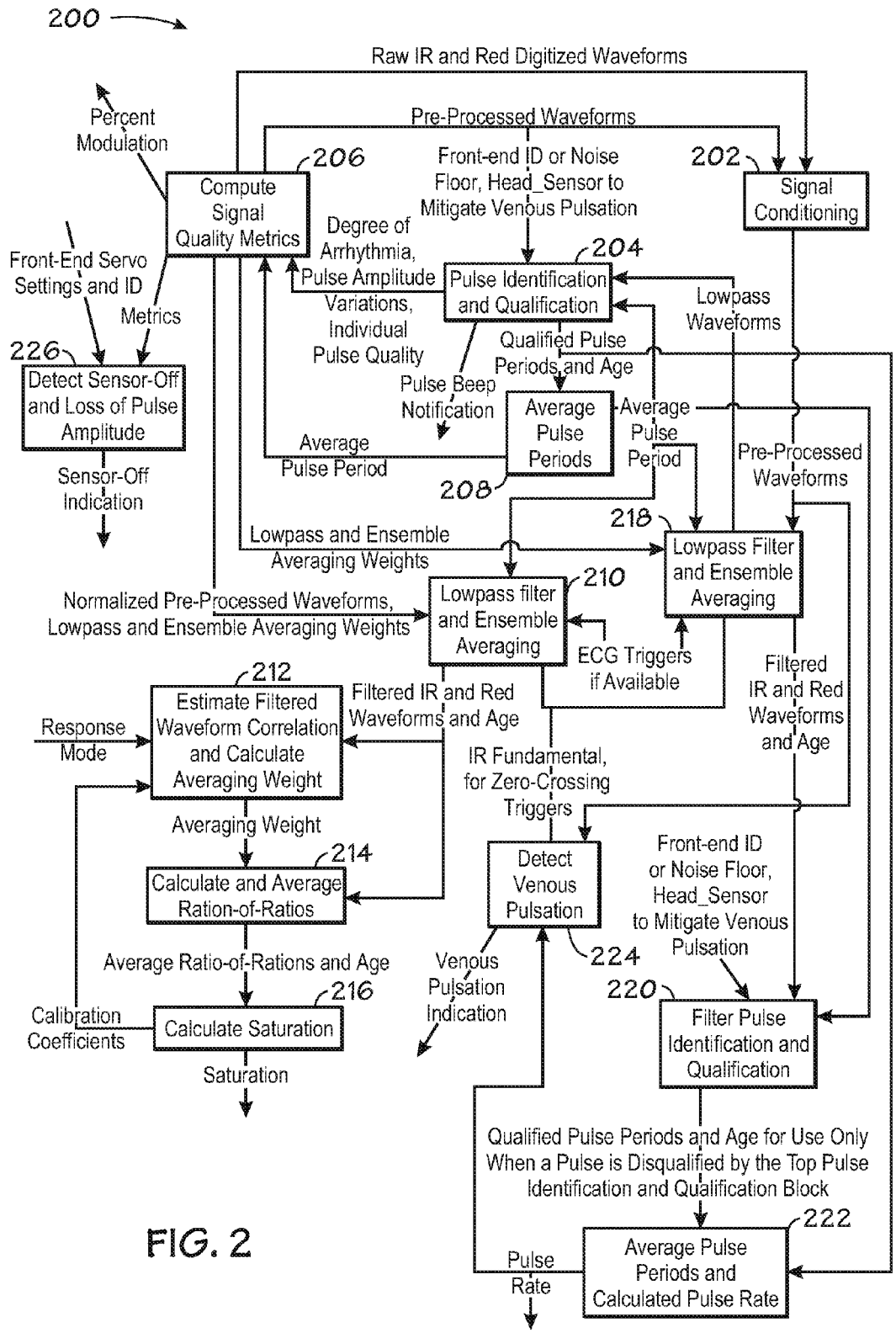
FIG. 2 is a block diagram of the signal processing architecture of a pulse oximeter in accordance with one embodiment of the present invention.

The brief description of an exemplary pulse oximeter set forth above, serves as a basis for describing the methods for adjusting ensemble averaging weights for an ensemble averager, which are described below, in conjunction with FIG. 2.

The embodiments of the present invention may be implemented as a part of a larger signal processing system used to process optical signals for the purposes of operating a pulse oximeter. Such a signal processing system is shown in FIG. 2, which is a block diagram 200 of a signal processing architecture of a pulse oximeter in accordance with one embodiment of the present invention. The signal processing architecture 200 in accordance with the embodiments of the present invention may be implemented as a software algorithm that is executed by a processor of a pulse oximeter. In addition to calculating oxygen saturation and pulse rate, the system 200 measures various signal metrics that are used to determine filter weighting coefficients. Signal metrics are things that indicate if a pulse is likely a plethysmograph or noise. Signal metrics may be related to, for example, frequency (is it in the range of a human heart rate), shape (is it shaped like a cardiac pulse), rise time, etc. The system shown in FIG. 2 calculates both the oxygen saturation, and the pulse rate. The system 200 is also used for detecting venous pulsation and sensor off and lost pulse conditions, which are described separately below.

I. Oxygen Saturation Calculation

Block 202 represents the operation of the Signal Conditioning block. The digitized red and IR signals or waveforms are received and are conditioned in this block by: (1) taking the $1^{st}$ derivative to get rid of baseline shift, (2) low pass filtering with fixed coefficients, and (3) dividing by a DC value to preserve the ratio. The function of the Signal Conditioning subsystem is to emphasize the higher frequencies that occur in the human plethysmograph and to attenuate low frequencies in which motion artifact is usually concentrated. The Signal Conditioning subsystem selects its filter coefficients (wide or narrow band) based on hardware characteristics identified during initialization. Inputs to block 202 are digitized red and IR signals, and its outputs are pre-processed red and IR signals.

Block 204 represents the operation of the Pulse Identification and Qualification block. The low pass filtered digitized red and IR signals are provided to this block to identify pulses, and qualify them as likely arterial pulses. This is done using a pre-trained neural net, and is primarily done on the IR signal. The pulse is identified by examining its amplitude, shape and frequency. An input to this block is the average pulse period from block 208. This function changes the upfront qualification using the pulse rate. The output of block 204 indicates the degree of arrhythmia and individual pulse quality. Inputs to block 204 are: (1) pre-processed red and IR signals, (2) Average pulse period, and (3) lowpass waveforms from the low pass filter. Outputs from block 204 include: (1) degree of arrhythmia, (2) pulse amplitude variations, (3) individual pulse quality, (4) pulse beep notification, and (5) qualified pulse periods and age.

Block 206 is used to compute signal quality metrics. This block (block 206) determines the pulse shape (e.g., derivative skew), period variability, pulse amplitude and variability, Ratio of Ratios variability, and frequency content relative to pulse rate. Inputs to block 206 include: (1) raw digitized red and IR signals, (2) degree of arrhythmia, individual pulse quality, pulse amplitude variation, (3) pre-processed red and IR signals, and (4) average pulse period. Outputs from block 206 include: (1) lowpass and ensemble averaging filter weights, (2) metrics for sensor off detector, (3) normalized pre-processed waveforms, and (4) percent modulation.

Block 208 computes average pulse periods. This block (block 208) calculates the average pulse period from the pulses received. Inputs to block 208 include: qualified pulse periods and age. An output from block 208 includes the average pulse period.

Block 210 represents the functioning of the lowpass filter and ensemble averaging subsystem. Block 210 low pass filters and ensemble averages normalized and preprocessed waveforms processed by block 206. The weights for the low pass filter are determined by the Signal Metrics block 206. The signal is also ensemble averaged (i.e., frequencies other than those of interest near the pulse rate and its harmonics are attenuated), with the ensemble averaging filter weights also determined by Signal Metrics block 206. Less weight is assigned if the signal is flagged as degraded. More weight is assigned if the signal is flagged as arrhythmic because ensemble-averaging is not appropriate during arrhythmia. Red and IR waveforms are processed separately, but with the same filtering weights. The filtering is delayed (e.g., approximately one second) to allow the signal metrics to be calculated first.

The filters use continuously variable weights. If samples are not to be ensemble-averaged, then the weighting for the previous filtered samples is set to zero in the weighted average, and the new samples are still processed through the algorithm. This block tracks the age of the signal and/or the accumulated amount of filtering (e.g., sum of response times and delays in processing). Too old a result will be flagged, if good pulses haven't been detected for a while. The inputs to block 210 include: (1) normalized pre-processed red and IR signals, (2) average pulse period, (3) low pass filter weights and ensemble averaging filter weights, (4) ECG triggers, if available, and (5) IR fundamental, for zero-crossing triggers. Outputs from block 210 include: (1) filtered red and IR signals, and (2) age.

Block 212 represents operations that estimate the ratio-of-ratios variance for the filtered waveforms and calculate averaging weights. The variable weighting for the filter is controlled by the ratio-of-ratios variance. The effect of this variable-weight filtering is that the ratio-of-ratios changes slowly as artifact increases and changes quickly as artifact decreases. The subsystem has two response modes, including fast and normal modes. For example, filtering in the fast mode targets an age metric of 3 seconds, and the target age may be 5 seconds in the normal mode. In the fast mode, the minimum weighting of the current value is clipped at a higher level. In other words, a low weight is assigned to the newest ratio-of-ratios calculation if there is noise present, and a high weight if no noise is present. The inputs to block 212 include: (1) filtered red and IR signals and age, (2) calibration coefficients, and (3) response mode (e.g., user speed settings). Outputs from block 212 include an averaging weight for ratio-of-ratios calculation. The averaging weight is used as an input to block 214 along with filtered IR and Red waveforms to calculate averaged ratio of ratios and age.

Block 216 represents operations that calculate oxygen saturation. Saturation is calculated using an algorithm with the calibration coefficients and averaged ratio of ratios. Inputs to block 116 include: (1) Averaged Ratio-of-Ratios, and (2) calibration coefficients. An output from block 216 is the oxygen saturation value.

II. Pulse Rate Calculation

Block 218 low pass filters and ensemble averages the signal(s) conditioned by block 202, for the pulse rate identification. The weights for the low pass filter are determined by the Signal Metrics block 206. The signal is also ensemble averaged (i.e., frequencies other than those of interest near the pulse rate and its harmonics are attenuated), with the ensemble averaging filter weights also determined by Signal Metrics block 206. Less weight is assigned if the signal is flagged as degraded. More weight is assigned if the signal is flagged as arrhythmic because ensemble-averaging is not appropriate during arrhythmia. Red and IR are processed separately. The filtering is delayed (e.g., approximately one second) to allow the signal metrics to be calculated first.

The filters use continuously variable weights. If samples are not to be ensemble-averaged, then the weighting for the previous filtered samples is set to zero in the weighted average, and the new samples are still processed through the algorithm. This block (block 218) tracks the age of the signal and/or the accumulated amount of filtering (sum of response times and delays in processing). Too old a result will be flagged (if good pulses haven't been detected for awhile). Inputs to block 218 include: (1) pre-processed red and IR signals, (2) average pulse period, (3) lowpass filter weights and ensemble averaging filter weights, (4) ECG triggers, if available, and (5) IR fundamental, for zero-crossing triggers. Outputs from block 218 include: (1) filtered red and IR signals and (2) age.

Block 220, or the Filtered Pulse Identification and Qualification block, calculates the pulse periods from the filtered waveforms, and its results are used only when a pulse is disqualified by block 204. Inputs to block 220 include: (1) filtered red and IR signals and age, (2) average pulse period, (3) hardware ID or noise floor, (4) and the kind or type of sensor that is used to detect the IR and Red energies. Output from block 220 includes qualified pulse periods and age.

Block 222, or the Average Pulse Periods and Calculate Pulse Rate block, calculates the pulse rate and average pulse period. This block (block 222) receives qualified pulse periods and age as inputs and provides: (1) average pulse period and (2) pulse rate as outputs.

III. Venous Pulsation

Block 224, or the Detect Venous Pulsation block receives as inputs the pre-processed red and IR signals and age from Block 202, and pulse rate and provides an indication of venous pulsation as an output. Block 224 also provides an IR fundamental waveform in the time domain using a single-tooth comb filter which is output to the Ensemble Averaging filters (e.g., block 210 and 218). Inputs to block 224 include: (1) filtered red and IR signals and age and (2) pulse rate. Outputs from block 124 include: an indication of venous pulsation and IR fundamental. In one embodiment, block 224 measures the "openness" of an IR-Red Lissajous plot to determine the whether a flag (e.g., Venous_Pulsation) should be set. The output flag (e.g., Venous_Pulsation) is updated periodically (e.g., every second). In addition, the IR fundamental waveform is output to the Ensemble Averaging filters.

IV. Sensor Off

Block 226, or the Detect Sensor-Off and Loss of Pulse Amplitude block, uses a pre-trained neural net to determine whether the sensor is off the surface of the blood-perfused tissue, for example, of a patient. The inputs to the neural net are metrics that quantify several aspects of the behavior of the IR and Red values over the last several seconds. Samples are ignored by many of the system 200's subsystems while the signal state is either not indicative of a pulse being present, or indicative that a sensor is not on a monitoring site (e.g., Pulse Present, Disconnect, Pulse Lost, Sensor May be Off, and Sensor Off). Inputs to block 226 include: (1) signal quality metrics, and (2) the oximeter's LED brightness, amplifier gain, and (3) an ID indicating the oximeter's hardware configuration. Outputs from block 226 include a signal state including sensor-off indication.

In the architecture 200 described above, the function of block 226, Pulse lost and Pulse Search indications, may be derived using information from several parts of the signal processing architecture. In addition, the signal processing architecture will not use the received IR and red waveforms to compute oxygen saturation or pulse rate if a valid sensor is not connected, or if the Sensor-Off or Loss of Pulse Amplitude are detected by the signal processing architecture.

The brief description of an embodiment of a pulse oximeter signal processing architecture in accordance with the present invention, set forth above, serves as a basis for describing the methods and devices that are directed towards the selection of ensemble averaging weights used for ensemble averaging of signals that correspond with detected waveforms from a pulse oximeter, as is generally indicated by blocks 210 and 218 above.

Ensemble Averaging Weights

As set forth above, the selection of ensemble averaging weights are based on one or more or a combination of various signal quality metrics or indicators. In particular, in one embodiment, the metrics that are used to adjust ensemble-averaging weight, includes a measure of the degree of arrhythmia. This metric is used to reduce the degree of ensemble-averaging when the patient appears to be arrhythmic, as ensemble-averaging works less well for signals having highly variable frequency content. Another metric used to adjust ensemble-averaging weight includes a measure of the degree of variability of ratio-of-ratios (e.g., lack of similarity or correlation between IR and Red waveforms). This metric is sensitive to the presence of motion or other noise sources. This metric is different from that of other known techniques such as Conlon's, in that Conlon teaches a metric that compares the similarity between current and previous-pulse waveforms, presumably from the same wavelength, but not the similarity between two simultaneous waveforms at different wavelengths. Another metric used to adjust ensemble-averaging weight includes a ratio of a current pulse amplitude to the long-term average pulse amplitude. A long-term average pulse amplitude refers to an average that has a response time of perhaps a minute when all pulses are qualified, and several times longer if most pulses are being disqualified. This metric is designed to capture the degree of motion artifact, similar to Conlon's, however, this metric is an analog metric, whereas Conlon's metric has just a few discrete states (e.g., no artifact, low artifact, high artifact). Another metric used to adjust ensemble-averaging weight includes a ratio of a current pulse amplitude to the previous pulse amplitude. This metric is used to quickly change the ensemble-averaging weight when large motion artifact start or stop. Another metric used to adjust ensemble-averaging weight includes a measure of the overall signal quality metric for a single pulse, which metric is itself a combination of several other metrics, including the metrics described above. This metric is used to quickly reduce the ensemble filtering when motion artifact subsides and the input waveform is presumed to be of better quality than a heavily ensemble-averaged waveform. Another metric used to adjust ensemble-averaging weight includes a ratio of a current pulse period to the average pulse period. This metric is used to reduce the ensemble filtering in the event that the heart skips a beat, which can happen occasionally on many people.

When the subsystem (210 and/or 218) is notified that the Pulse Identification and Qualification subsystem (204) has just completed evaluation of a potential pulse, the subsystem updates ensemble-averaging weights, used by the instances of the Ensemble Averaging subsystem. Separate weights are computed for the two Ensemble Averaging instances whose outputs are used in computing saturation and pulse rate. These weights are based in part on metrics provided by the instance of the Pulse Identification and Qualification subsystem whose input waveforms have not been ensemble averaged.

The equations for Sat_Ensemble_Averaging_Filter_Weight are as follows:

$$x=\max(\text{Short\_RoR\_Variance}, \text{Pulse\_Qual\_RoR\_Variance}/1.5)*\max(\text{Long\_Term\_Pulse\_Amp\_Ratio}, 1.0)$$

$$\text{RoR\_Variance\_Based\_Filt\_Wt} = 0.5*0.05/\max(0.05, x)$$

$$\text{Arr\_Prob} = (\text{Period\_Var} - 0.1*\text{Short\_RoR\_Variance} - 0.09)/(0.25-0.09);$$

$$\text{Arr\_Min\_Filt\_Wt\_For\_Sat} = 0.05 + 0.5*\text{bound}(\text{Arr\_Prob}, 0, 1.0)$$

$$\text{Sat\_Ensemble\_Averaging\_Filter\_Weight} = \max(\text{RoR\_Variance\_Based\_Filt\_Wt}, \text{Arr\_Min\_Filt\_Wt\_For\_Sat})*(1.0+\text{Pulse\_Qual\_Score})$$

$$\text{Sat\_Ensemble\_Averaging\_Filter\_Weight} = \min(\text{Sat\_Ensemble\_Averaging\_Filter\_Weight}, 1.0),$$

where bound(a,b,c) denotes min(max(a,b),c)

The above equations result in a default weight of 0.5 for low values of the Ratio-of-Ratios variances. Short_RoR_Variance and Pulse_Qual_RoR_Variance are both computed over a time interval (e.g., a three-second interval). The interval for Pulse_Qual_RoR_Variance ends with the qualification or rejection of the most recent pulse, which would usually include the most recent samples. The weight is reduced by high Ratio-of-Ratios variances, and by high values of Long_Term_Pulse_Amp_Ratio that would typically indicate motion artifact. Arr_Min_Filt_Wt_For_Sat imposes a minimum value on the ensemble-averaging weight (range 0.05-0.55) based primarily on Period_Var, which quantifies the degree of arrhythmia. This is done because ensemble-averaging is less effective for pulses having dissimilar periods. If the most recent pulse received a good Pulse_Qual_Score, this can increase the maximum value of Sat_Ensemble_Averaging_Filter_Weight from 0.5 to 1.0.

The equations for Rate_Ensemble_Averaging_Filter_Weight are as follows:

$$\text{Arr\_Prob} = (\text{Period\_Var} - 0.07)/(0.20-0.07)$$

$$\text{Arr\_Min\_Filt\_Wt\_For\_Rate} = 0.05 + 0.5*\text{bound}(\text{Arr\_Prob}, 0, 1.0)$$

$$x = \max(\text{RoR\_Variance\_Based\_Filt\_Wt}, \text{Arr\_Min\_Filt\_Wt\_For\_Rate})*(1.0+\text{Pulse\_Qual\_Score})$$

if
   Short_Term_Pulse_Amp_Ratio*Long_Term_Pulse_Amp_Ratio<1.0

$$x = x/\text{Short\_Term\_Pulse\_Amp\_Ratio}$$

if Avg_Period>0

$$x = x*\text{bound}(\text{Pulse\_Qual\_Score}*\text{Qualified\_Pulse\_Period}/\text{Avg\_Period}, 1.0, 3.0)$$

$$\text{Rate\_Ensemble\_Averaging\_Filter\_Weight} = \min(x, 1.0)$$

These equations differ from the ones for Sat_Ensemble_Averaging_Filter_Weight as follows:

a) The thresholds used to compute Arr_Prob are somewhat lower, because it is desirable that arrhythmic pulses not be obscured by ensemble averaging prior to pulse qualification.
b) Small values of Short_Term_Pulse_Amp_Ratio typically indicate that motion artifact has just subsided, which means that the ensemble-averaging weight may be quickly increased. This has been found empirically to be beneficial for pulse qualification, but not for ratio-of-ratios filtering and saturation computation.
c) If the heart skips a beat, with or without prior arrhythmia, the longer-than-average Qualified_Pulse_Period that results will increase the ensemble-averaging weight, so as not to obscure the skipped beat from subsequent pulse qualification.

In one aspect, the ensemble averaging weights that have been determined as described above, are used for two separate ensemble averagers for processing a detected waveform for use in calculating oxygen saturation and a pulse rate. The ensemble averager used for calculating oxygen saturation operates on a signal which has been normalized, while the ensemble averager for the pulse rate calculation operates on a signal which has not been normalized. A pulse oximeter with separate ensemble averaging for oxygen saturation and heart rate is described in a co-pending patent application assigned to the assignee herein, and titled: Pulse Oxiemter with Separate Ensemble Averaging for Oxygen Saturation and Heart Rate, Ser. No. 10/796,578, is hereby incorporated herein by reference, in its entirety for all purposes. In that patent application, the metrics chosen for the two paths through the two ensemble averagers can be varied to optimize the ensemble averaging for oxygen saturation or pulse rate calculations. For example, a lower threshold is used for a metric to detect arrhythmic pulses when used to calculate pulse rate, as compared to calculating oxygen saturation. Also, a metric for a short term pulse amplitude ratio will be small when motion artifact has just subsided, and this is given more weight in the pulse rate calculation than in the oxygen saturation calculation.

DEFINITIONS

Data Inputs

Avg_Period—Average pulse period reported by Pulse Rate Calculation subsystem.

Long_Term_Pulse_Amp_Ratio—Quantifies last pulse amplitude compared to historic pulse amplitude. Provided by the Pulse Identification and Qualification subsystem. Values substantially larger than 1.0 are typically indicative of motion artifact, and result in lower Ensemble_Averaging_Filter_Weights.

Period_Var—Period-variability metric from the Pulse Identification and Qualification subsystem. Used to gauge the extent of arrhythmia. For instance, a value of 0.10 would indicate that the average difference between consecutive pulse periods is 10% of Avg_Period.

Pulse_Qual_RoR_Variance—RoR_Variance metric from the Pulse Identification and Qualification subsystem.

Pulse_Qual_Score—Score computed by the pulse qualification neural net in the Pulse Identification and Qualification subsystem. Zero is extremely poor and 1.0 is excellent.

Qualified_Pulse_Period—Most recent pulse period qualified by the Pulse Identification and Qualification subsystem.

Short_Term_Pulse_Amp_Ratio—Quantifies last pulse amplitude compared to previous pulse amplitude.

Outputs

Frequency_Ratio—Ratio of Mean_IR_Frequency_Content to pulse rate.

LPF_RoR_Variance—Quantifies variability of ratio-of-ratios. Computed over a 9-second window from LPF_Scaled_Waveforms.

Rate_LPF_Weight—Lowpass filter weight to be used by the instance of the Ensemble Averaging subsystem that preprocesses waveforms used for pulse qualification and pulse rate calculation.

RoR_Variance—Quantifies variability of ratio-of-ratios. Computed over a 9-second window from Scaled_Waveforms. For example, a value of 0.10 would indicate that sample-to-sample ratio-of-ratios values differ from the mean ratio-of-ratios value by an average of 10% of the mean ratio-of-ratios value.

Sat_Ensemble_Averaging_Filter_Weight—Ensemble-averaging weight to be used by the instance of the Ensemble Averaging subsystem that preprocesses waveforms used for pulse qualification and pulse rate calculation.

Sat_LPF_Weight—Lowpass filter weight to be used by the instance of the Ensemble Averaging subsystem that preprocesses waveforms used for pulse qualification and pulse rate calculation.

Scaled_Waveforms—Scaled versions of IR and Red Pre_Processed_Waveforms.

Short_RoR_Variance—Quantifies variability of ratio-of-ratios. Computed over a 3-second window from Scaled_Waveforms.

Internal Variables

Arr_Prob—Likelihood of arrhythmia that would limit the amount of ensemble averaging. Based on Period_Var, with threshold that are specific to each of the two Ensemble Averaging_Filter_Weights.

Arr_Min_Filt_Wt_For_Rate, Arr_Min_Filt_Wt_For_Sat—Minimum values for the two Ensemble_Averaging_Filter_Weights, based on their respective Arr_Prob values.

LPF_Scaled_Waveforms—Lowpass-filtered version of Scaled_Waveforms, used to compute LPF_RoR_Variance.

Mean_IR_Frequency_Content—Estimate of mean frequency content of the IR input waveform. Used to compute Frequency_Ratio metric.

RoR_Variance_Based_Filt_Wt—Component for Ensemble_Averaging_Filter_Weights based on RoR_Variance metrics and Long_Term_Pulse_Amp_Ratio.

Accordingly, as will be understood by those of skill in the art, the present invention which is related to the selection of ensemble averaging weights, may be embodied in other specific forms without departing from the essential characteristics thereof. For example, while the present embodiments have been described in the time-domain, frequency-based methods are equally relevant to the embodiments of the present invention. Accordingly, the foregoing disclosure is intended to be illustrative, but not limiting, of the scope of the invention, which is set forth in the following claims.

What is claimed is:

1. A pulse oximeter, comprising:
 a signal processing architecture comprising:
  a signal conditioner configured to receive light waveforms and provide conditioned light waveforms with attenuated low frequencies associated with motion artifact and emphasized high frequencies associated with a human plethysmograph;
  a signal metrics calculator configured to compute signal quality metrics of the light waveforms based on characteristics of the light waveforms and based on the conditioned light waveforms;

an ensemble averager configured to ensemble average the conditioned light waveforms with continuously variable ensemble averaging weights based on the signal quality metrics to provide filtered light waveforms; and a filtered pulse identifier and qualifier configured to receive the filtered light waveforms and identify qualified pulse periods based on the filtered light waveforms.

2. The pulse oximeter of claim 1, wherein the signal processing architecture comprises a pulse rate calculator configured to receive data regarding the qualified pulse periods and calculate a pulse rate and average pulse period.

3. The pulse oximeter of claim 1, wherein the signal processing architecture comprises a low pass filter configured to receive and low pass filter the conditioned light waveforms with continuously variable low pass filter weights based on the signal quality metrics.

4. The pulse oximeter of claim 1, wherein the signal metrics calculator is configured to provide an indication of whether the light waveforms are degraded based on the characteristics.

5. The pulse oximeter of claim 4, wherein the characteristics comprise pulse shape, period variability, pulse amplitude, pulse variability, ratio of ratios variability, frequency content relative to pulse rate, or any combination thereof.

6. The pulse oximeter of claim 4, wherein the continuously variable ensemble averaging weights are devalued when the light waveforms are indicated as degraded.

7. The pulse oximeter of claim 1, wherein the signal conditioner is configured to receive digitized red light waveforms and digitized infrared light waveforms.

8. The pulse oximeter of claim 1, wherein the ensemble averager is configured to track an age of the light waveforms and/or an accumulated amount of filtering.

9. The pulse oximeter of claim 8, wherein the ensemble averager is configured to flag data associated with light waveforms with an age value that exceeds a threshold.

10. A pulse oximeter system, comprising:
a processor and circuitry configured to:
receive light waveforms from a sensor;
determine at least one signal quality metric for the light waveforms;
calculate at least one weight using a continuously variable weighting function based on the at least one signal quality metric; and
ensemble average the light waveforms using the at least one calculated weight to provide a pulse rate calculation or blood oxygenation calculation.

11. The pulse oximeter system of claim 10, comprising the sensor, wherein the sensor is configured to receive first and second light waveforms from tissue, and wherein the first and second light waveforms correspond to two different wavelengths of light.

12. The pulse oximeter system of claim 11, wherein the first light waveform corresponds to a red wavelength and the second light waveform corresponds to an infrared wavelength.

13. The pulse oximeter system of claim 10, wherein the processor and circuitry are configured to measure a degree of variability of a ratio of ratios of the light waveforms to determine the at least one signal quality metric.

14. The pulse oximeter system of claim 10, wherein the signal quality metric determination is based on pulse shape, period variability, pulse amplitude, pulse variability, ratio of ratios variability, frequency content relative to pulse rate, or any combination thereof.

15. A method of ensemble averaging signals in a pulse oximeter system, comprising:
receiving light waveforms from a sensor into a signal processor of a pulse oximeter;
determining at least one signal quality metric for the light waveforms with the signal processor;
calculating at least one weight with the signal processor using a continuously variable weighting function based on the at least one signal quality metric; and
ensemble averaging the light waveforms with the signal processor using the at least one calculated weight to provide a pulse rate calculation or blood oxygenation calculation.

16. The method of claim 15, comprising emitting light waveforms from an emitter of a sensor and detecting the light waveforms with a detector of the sensor.

17. The method of claim 15, wherein determining the at least one signal quality metric comprises identifying whether at least a portion of the light waveforms are noise.

18. The method of claim 15, wherein determining the at least one signal quality metric comprises analyzing frequency, shape, and/or rise time of the light waveforms.

19. The method of claim 15, comprising identifying pulses based on the light waveforms and analyzing the pulses to determine whether the pulses are arterial pulses.

20. The method of claim 15, comprising monitoring an age of the light waveforms and flagging data associated with light waveforms over a certain age.

* * * * *